United States Patent [19]

Berenyi née Poldermann et al.

[11] 4,303,660
[45] Dec. 1, 1981

[54] PYRAZOLO[1,5-C]QUINAZOLINE DERIVATIVES AND ANALGESIC COMPOSITIONS CONTAINING THEM

[75] Inventors: Edit Berényi née Poldermann; Enikó Szirt née Kiszelly; Péter Görög; Lujza Petócz; Ibolya Kosóczky; Ágnes Kovács née Palotai; Gabriella Ürmös née Lassu, all of Budapest, Hungary

[73] Assignee: Egyt Gyogyszervegyeszeti Gyar, Budapest, Hungary

[21] Appl. No.: 150,349

[22] Filed: May 16, 1980

[30] Foreign Application Priority Data

May 18, 1979 [HU] Hungary .............................. EE 2663

[51] Int. Cl.³ .................. A61K 31/505; C07D 487/04
[52] U.S. Cl. ..................................... 424/251; 542/415;
542/415; 542/458; 542/405; 544/231; 544/250
[58] Field of Search ................ 544/250, 231; 424/251;
542/415, 405, 458

[56] References Cited

U.S. PATENT DOCUMENTS

| | | | |
|---|---|---|---|
| 3,313,815 | 4/1967 | Wolfe et al. | 544/250 |
| 3,531,482 | 9/1970 | Ott | 544/250 X |
| 4,110,452 | 8/1978 | Rovnyak et al. | 424/251 |
| 4,112,098 | 9/1978 | Vogt | 424/251 |
| 4,198,412 | 4/1980 | Vogt et al. | 424/251 |

OTHER PUBLICATIONS

Nuller, W. B. Saunders Co; Chemistry of Organic Compounds, Philadelphia, 1965, pp. 516–17.

*Primary Examiner*—Donald G. Daus
*Assistant Examiner*—Diana G. Rivers
*Attorney, Agent, or Firm*—Young & Thompson

[57] ABSTRACT

The invention relates to novel pyrazolo[1,5-c]quinazoline derivatives of the general formula I

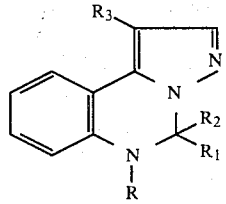

(XIX)

wherein
  R represents a hydrogen atom, a $C_{1-4}$ alkyl group or an acyl group,
  $R_1$ represents a hydrogen atom, a $C_{1-12}$ alkyl group, a $C_{3-8}$ cycloalkyl group, a $C_{2-4}$ alkenyl group, an aralkyl group, wherein the alkyl group has 1 to 4 carbon atoms, a phenylalkenyl group, wherein the alkenyl group has 2 to 4 carbon atoms, furthermore a carboxy group or a phenyl group optionally substituted by one or more substituents selected from the group consisting of halogen, hydroxy, $C_{1-4}$ alkoxy, nitro or di($C_{1-4}$ alkyl)amino groups, or
  R and $R_1$ may form together a valence bond,
  $R_2$ represents a hydrogen atom, a $C_{1-4}$ alkyl or a phenyl group, or
  $R_1$ and $R_2$ may form together a $C_{2-7}$ alkylene group,
  $R_3$ represents a nitro group, an amino group, an alkylamino group, a dialkylamino group, wherein the alkyl groups have 1 to 4 carbon atoms, an alkylideneimino group, wherein the alkylidene group has 1 to 4 carbon atoms, a benzylideneimino group or an acylamino group,
  and pharmaceutically acceptable acid addition salts thereof.

The novel compounds of the general formula I can be employed primarily as analgesic agents.

16 Claims, No Drawings

PYRAZOLO[1,5-C]QUINAZOLINE DERIVATIVES AND ANALGESIC COMPOSITIONS CONTAINING THEM

This invention relates to novel pyrazolo[1,5-c]quinazoline derivatives, their preparation and compositions containing them.

More particularly, the invention relates to novel pyrazolo[1,5-c]quinazoline compounds having the general formula I

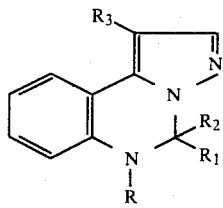
(XIX)

wherein
R represents a hydrogen atom, a $C_{1-4}$ alkyl group or an acyl group,
$R_1$ represents a hydrogen atom, a $C_{1-12}$ alkyl group, a $C_{3-8}$ cycloalkyl group, a $C_{2-4}$ alkenyl group, an aralkyl group, wherein the alkyl group has 1 to 4 carbon atoms, a phenylalkyl group, wherein the alkenyl group has 2 to 4 carbon atoms, furthermore a carboxy group or a phenyl group optionally substituted by one or more substituents selected from the group consisting of halogen, hydroxy, $C_{1-4}$ alkoxy, nitro or di($C_{1-4}$ alkyl)amino groups, or
R and $R_1$ may form together a valence bond,
$R_2$ represents a hydrogen atom, a $C_{1-4}$ alkyl or a phenyl group, or
$R_1$ and $R_2$ may form together a $C_{2-7}$ alkylene group,
$R_3$ represents a nitro group, an amino group, an alkylamino group, a dialkylamino group, wherein the alkyl groups have 1 to 4 carbon atoms, an alkylideneimino group, wherein the alkylidene group has 1 to 4 carbon atoms, a benzylideneimino group or an acylamino group,
and pharmaceutically acceptable acid addition salts thereof.

The novel compounds can be employed primarily as analgesic agents.

Compounds having pyrazolo[1,5-c]quinazoline basic structure are known from the literature. Thus, 5-aminopyrazolo[1,5-c]quinazoline derivatives having antiphlogistic effects [U.S. Pat. No. 3,531,482], pyrazolo[1,5-c]quinazoline-5(6H)- one derivatives possessing antiphlogistic and immunosuppressive effects [U.S. Pat. No. 3,897,434] as well as pyrazolo[1,5-c]quinazoline derivatives having antihistamine and antiphlogistic effects [Belgian Pat. No. 856,386] have been already described. However, the pyrazolo[1,5-c]quinazoline derivatives of the general formula I are novel compounds.

In the general formula I a $C_{1-4}$ alkyl group is a methyl, ethyl, n-propyl, isopropyl, n-butyl, sec.-butyl, tert.-butyl or isobutyl group.

An acyl group is preferably an alkanoyl group, such as formyl, acetyl, propionyl, etc., an aroyl group, such as benzoyl, substituted benzoyl, etc. or an aralkanoyl group, such as phenylacetyl etc.

A $C_{1-12}$ alkyl group means a linear or branched chain alkyl group, such as a methyl, ethyl, n-propyl, isopropyl, n-butyl, sec.-butyl, tert.-butyl, isobutyl, pentyl, hexyl, heptyl, octyl, nonyl, decyl, undecyl or dodecyl group.

A $C_{3-8}$ cycloalkyl group is a cyclopropyl, cyclobutyl, cyclopentyl, cyclohexyl, cycloheptyl or cyclooctyl group, especially a cyclohexyl group.

A $C_{2-4}$ alkenyl group is preferably a propenyl or butenyl group.

An aralkyl group is preferably a benzyl or phenylethyl group.

A phenylalkenyl group is preferably a phenylpropenyl or phenylbutenyl group, especially a styryl group.

A substituted phenyl group is preferably a nitrophenyl, methoxyphenyl, hydroxyphenyl, halogenphenyl, such as chlorophenyl or bromophenyl, N,N-dimethylaminophenyl or N,N-diethylaminophenyl group.

When $R_1$ and $R_2$ form together a $C_{2-7}$ alkylene group, a 3- to 8-membered alicyclic ring, such as cyclopropane, cyclopentane, cyclohexane, cycloheptane or cyclooctane ring is produced.

The alkylideneimino group is an ethylideneimino, isopropylideneimino or butylideneimino group, especially an isopropylideneimino group.

The pharmaceutically acceptable acid addition salt can be an inorganic acid addition salt, such as sulfate, hydrochloride, hydrobromide, etc. or an organic acid additon salt, such as acetate, fumarate, maleate, citrate, lactate, etc.

A subclass of the compounds of the invention consists of the nitropyrazolo[1,5-c]quinazoline derivatives of the general formula Ia

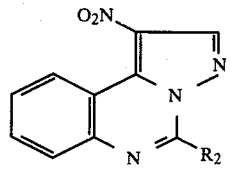
(Ia)

wherein $R_2$ is as stated above, and the pharmaceutically acceptable acid addition salts thereof. Preferably, $R_2$ represents a hydrogen atom or a $C_{1-4}$ alkyl group.

A further subclass of the compounds of the invention consists of the aminopyrazolo[1,5-c]quinazoline derivatives of the general formula Ib

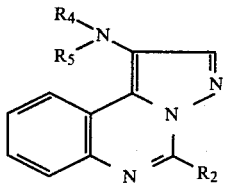
(Ib)

wherein $R_2$ is as stated above, $R_4$ represents a hydrogen atom, a $C_{1-4}$ alkyl group or an acyl group, $R_5$ represents a hydrogen atom or a $C_{1-4}$ alkyl group or $R_4$ and $R_5$ form together a $C_{1-4}$ alkylidene group, and the pharmaceutically acceptable acid addition salts thereof.

Preferably, $R_2$ represents a hydrogen atom or a $C_{1-4}$ alkyl group, $R_5$ stands for a hydrogen atom and $R_4$ is a $C_{1-4}$ alkanoyl group.

The compounds of the invention include also the nitropyrazolo[1,5-c]quinazoline derivatives of the general formula Ic

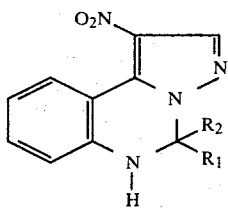

(Ic)

wherein $R_1$ and $R_2$ are as stated above, and the pharmaceutically acceptable acid addition salts thereof. Preferably, $R_1$ and $R_2$ each represents a hydrogen atom.

A still further subclass of the compounds of the invention includes the nitropyrazolo[1,5-c]quinazoline derivatives of the general formula Id

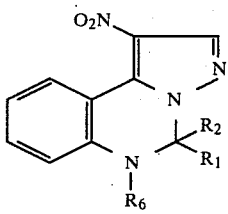

(Id)

wherein $R_1$ and $R_2$ are as stated above, $R_6$ represents a $C_{1-4}$ alkyl group or an acyl group, and the pharmaceutically acceptable acid addition salts thereof.

Preferably, $R_1$ represents a $C_{1-4}$ alkyl group, $R_2$ stands for a hydrogen atom or a $C_{1-4}$ alkyl group and $R_6$ represents a a $C_{1-4}$ alkanoyl group, such as an acetyl group.

An additional subclass of the compounds of the invention includes the aminopyrazolo[1,5-c]quinazoline derivatives of the general formula If

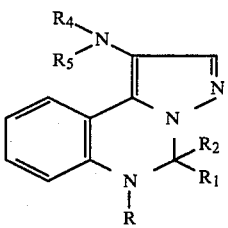

(If)

wherein R, $R_1$, $R_2$, $R_4$ and $R_5$ are as stated above, and the pharmaceutically acceptable acid addition salts thereof.

Preferably, R represents a hydrogen atom or a $C_{1-4}$ alkanoyl group, $R_1$ and $R_2$ each stands for a $C_{1-4}$ alkyl group, $R_5$ is a hydrogen atom and $R_4$ represents a $C_{1-4}$ alkanoyl group.

Preferred pyrazolo[1,5-c]quinazoline derivatives of the invention are as follows:

1-nitropyrazolo[1,5-c]quinazoline,
1-nitro-5-methylpyrazolo[1,5-c]quinazoline,
1-acetaminopyrazolo[1,5-c]quinazoline,
1-nitro-5-methyl-6-acetyl-5,6-dihydropyrazolo[1,5-c]quinazoline,
1-nitro-5,5-dimethyl-6-acetyl-5,6-dihydropyrazolo[1,5-c]quinazoline,
1-acetamino-5,5-dimethyl-5,6-dihydropyrazolo[1,5-d]quinazoline,
1-acetamino-5,5-dimethyl-6-acetyl-5,6-dihydropyrazolo[1,5-c]quinazoline,
1-acetamino-5-methyl-6-acetyl-5,6-dihydropyrazolo[1,5-c]quinazoline,
1-acetamino-5-methylpyrazolo[1,5-c]quinazoline.

The novel compounds of the general formula I and their pharmaceutically acceptable acid addition salts are prepared as follows:

(a) for the preparation of a nitropyrazolo[1,5-c]quinazoline of the general formula Ia, wherein $R_2$ has the same meaning as given in relation to the general formula I, the pyrazole derivative of the formula II

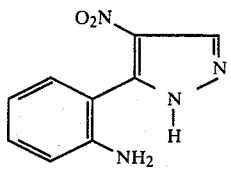

(II)

is reacted with an orthoformate of the general formula III $$R_2-C(OAlk)_3 \quad (III)$$

wherein Alk represents a $C_{1-4}$ alkyl group and $R_2$ is as stated above, or with a carboxylic halogenide of the general formula IV

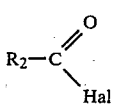

(IV)

wherein $R_2$ is as stated above and Hal represents a halogen atom, or with a carboxylic anhydride of the general formula V $$(R_2\text{-CO})_2O \quad (V)$$

wherein $R_2$ is as stated above; or (b) for the preparation of an aminopyrazolo[1,5-c]quinazoline of the general formula Ib, wherein $R_2$ has the same meaning as given in relation to the general formula I, $R_4$ represents a hydrogen atom, a $C_{1-4}$ alkyl group or an acyl group, $R_5$ represents a hydrogen atom or a $C_{1-4}$ alkyl group or $R_4$ and $R_5$ form together a $C_{1-4}$ alkylidene group, a compound of the general formula Ia, wherein $R_2$ is a stated above, is reacted with a reducing agent or catalytically hydrogenated, and, if desired, an obtained compound of the general formula Ib, wherein $R_2$ is as stated above, $R_4$ and $R_5$ each represents a hydrogen atom, is alkylated with a $C_{1-4}$ alkyl halogenide or a $C_{1-4}$ alkyl sulfate, or acylated with a carboxylic acid or an active acylating derivative thereof, or condensed with a $C_{1-4}$ aliphatic aldehyde or a $C_{3-4}$ aliphatic ketone; or (c) for the preparation of a nitropyrazolo[1,5-c]quinazoline of the general formula Ic, wherein $R_2$ represents a hydrogen atom, $R_1$ has the same meaning as defined in relation to the general formula I, the pyrazole derivative of the formula II is reacted with an aldehyde of the general formula IV $$R_1-CHO \quad (VI)$$

wherein $R_2$ is as stated above; or (d) for the preparation of a nitropyrazolo[1,5-c]quinazoline of the general formula Ic, wherein $R_1$ and $R_2$ have the same meaning as defined in relation to the general formula I, the pyrazole derivative of the formula II is reacted with a ketone of the general formula VII

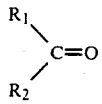

wherein $R_1$ and $R_2$ are as stated above; or (e) for the preparation of a nitropyrazolo[1,5-c]quinazoline of the general formula Id, wherein $R_1$ and $R_2$ have the same meaning as defined in relation to the general formula I, $R_6$ represents a $C_{1-4}$ alkyl group or an acyl group, a compound of the general formula Ic, wherein $R_1$ and $R_2$ are as stated above, is alkylated with a $C_{1-4}$ alkyl halogenide or $C_{1-4}$ alkyl sulfate or acylated with a carboxylic acid or an active acylating derivative thereof; or (f) for the preparation of an aminopyrazolo[1,5-c]quinazoline of the general formula If, wherein R, $R_1$ and $R_2$ have the same meaning as defined in relation to the general formula I and $R_4$ and $R_5$ are as stated in process variant (b), a compound of the general formula Ie

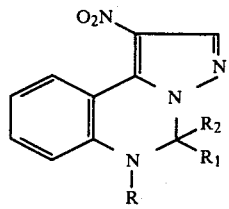

wherein R, $R_1$ and $R_2$ are as stated above, is reacted with a reducing agent or catalytically hydrogenated, and, if desired, an obtained compound of the general formula If, wherein R, $R_1$ and $R_2$ are as stated above, and $R_4$ and $R_5$ each represents a hydrogen atom, is alkylated with a $C_{1-4}$ alkyl halogenide or $C_{1-4}$ alkyl sulfate, or acylated with a carboxylic acid or an active acylating derivative thereof, or condensed with a $C_{1-4}$ aliphatic aldehyde or $C_{3-4}$ aliphatic ketone; or (g) for the preparation of an aminopyrazolo[1,5-c]quinazoline compound of the general formula Ih

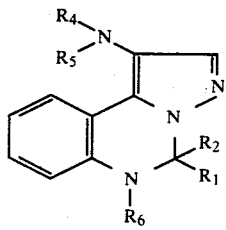

wherein $R_1$ and $R_2$ have the meanings as defined in relation to the general formula I, $R_4$ and $R_5$ are as given in process variant b, and $R_6$ is as stated in process variant (e), a compound of the general formula Ig

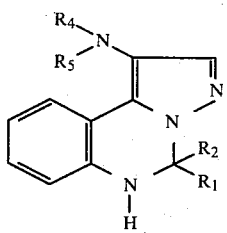

wherein $R_1$, $R_2$, $R_4$ and $R_5$ are as stated above, is alkylated with a $C_{1-4}$ alkyl halogenide or a $C_{1-4}$ alkyl sulfate, or acylated with a carboxylic acid or an active acylating derivative thereof;

and, if desired, any compound of the general formula I is converted with an inorganic or organic acid into its acid addition salt, or the compound of the general formula I is liberated from its acid addition salt with a base.

In process variant (a) of the invention, when 5-(o-aminophenyl)-4-nitropyrazole is reacted with an alkyl orthoformate of the general formula III, the latter compound is preferably used in an excess. The alkanol that forms during the reaction is removed continuously, in general. It is advantageous if the reaction temperature is higher than the boiling point of the alkanol formed, but lower than the boiling point of the orthoformate employed. The reaction rate can be enhanced by means of a catalyst, such as an inorganic or organic acid, e.g. hydrochloric acid, sulfuric acid or p-toluenesulfonic acid.

The above reaction can be performed in the presence of a solvent, such as an aromatic hydrocarbon, e.g. benzene, toluene or xylene, too.

The 5-(o-aminophenyl)-4-nitropyrazole is reacted with a carboxylic halogenide of the general formula IV preferably in the presence of an acid binding agent, such as pyridine or triethylamine. The acid binding agent can be simultaneously used as a solvent or diluent, too. A further possibility is to perform the reaction in the presence of an inert solvent, preferably an aromatic hydrocarbon. In general, the reaction temperature is from 0° C. to the boiling point of the solvent used. As a carboxylic halogenide of the general formula IV the carboxylic chloride or bromide are preferred.

When the starting compound of the formula II is reacted with a carboxylic anhydride of the general formula V, the latter compound is employed in an equimolar quantity or in an excess. The reaction temperature is from 20° to 200° C., especially at the boiling point of the carboxylic acid anhydride used.

In process variants (c) and (d) of the invention, the starting compound of the formula II is reacted with an aldehyde of the general formula VI or a ketone of the general formula VII preferably in the presence of a solvent, such as water, a polar organic solvent, e.g. methanol, ethanol, formic acid, acetic acid, etc. Mixtures of polar solvents can be used, too.

The reaction components of the general formula VI or VII can be used in excess. In this case they have the function of the solvent, too. The reaction temperature is, in general, from 0° C. to the boiling point of the solvent used. The reaction rate can be enhanced by employing a catalyst, such as acids.

In process variants (b) and (f) of the invention, the nitropyrazolo[1,5-c]quinazolines of the general formulae Ia and Ie are preferably reduced by catalytic hydrogenation in an inert solvent such as an alkanol. The catalyst may be Raney nickel, palladium/carbon or platinum dioxide. Of course, the compounds of the general formulae Ia and Ie may be reduced by any conventional method suitable for the reduction of nitro compounds.

In process variants (b), (e), (f) and (g), the active acylating derivative of a carboxylic acid is a compound suitable for the acetylation of the nitrogen atom, such as a carboxylic halogenide, e.g. chloride or bromide, a carboxylic ester, an activated carboxylic ester, a carboxylic anhydride or a mixed anhydride.

The starting 5-(o-aminophenyl)-4-nitropyrazole of the formula II can be prepared from 4-chloro-3-nitroquinoline by adapting Alberi's method [Gazz. chim. ital., 87, 772 (1957)].

The novel compounds of the general formula I have shown biological activities in several pharmacological tests. Thus, the novel compounds exert valuable analgesic effects, furthermore, inhibit the secretion of gastric acid and possess antiperistaltic effects.

The acute toxicity of the pyrazolo[1,5-c]quinazoline derivatives of the general formula I were determined on mice weighing 18 to 22 g. The compounds were administered orally. The $LD_{50}$ values are summarized in Table I.

TABLE I

| Acute toxicity | |
|---|---|
| Compound (No. of Example) | $LD_{50}$ p.o. mg/kg |
| 1 | 2000 |
| 3 | 2000 |
| 5 | 2000 |
| 9 | 2000 |
| 27 | 2000 |
| 31 | 2000 |
| 33 | 2000 |
| 34 | 2000 |
| 35 | 2000 |
| 36 | 1800 |

The analgesic activity was studied by means of the acetic acid writhing test on mice. After the intraperitoneal administration of 0.4 ml of 0.5 percent acetic acid, the writhing responses were counted between the 5 and 10 minutes. The writhing number was calculated as the percentage of the control value. The compounds tested were orally administered to the animals 1 hour prior to the treatment with acetic acid. The control group was treated orally with a carrier without active substance. The results obtained are summarized in Table II in which the values of $ED_{50}$ and therapeutic index of the test compounds as well as the reference substances are given. Paracetamole [p-hydroxyacetanilide] and phenylbutazon [4-butyl-1,2-diphenylpyrazolidine-3,5-dione] were used as reference substance.

TABLE II

| Analgesic activity test | | |
|---|---|---|
| Compound (No. of Example) | $ED_{50}$ p.o. mg/kg | Therapeutic index |
| 1 | 50 | 40 |
| 34 | 25 | 80 |
| paracetamole | 180 | 2,8 |
| phenylbutazon | 60 | 16,6 |

The influence of the compounds of the invention on the gastric acid secretion was studied on rats weighing 170 to 260 g according to Shay [Gastroenterology, 5, 43 (1945)]. The results obtained with both female and male rats after starvation are summarized in Table III. The following reference substances were used:

atropine, proglumide [D,L-4-benzamido-N,N-dipropylglutaramic acid] and cimetidine [1-methyl-3-[2-(5-methylimidazol-4-yl-methylthio)ethyl]guanidine-2-carbonitrile].

TABLE III

| Inhibition of the gastric acid secretion | | | |
|---|---|---|---|
| Compound (No. of Example) | Dosis, p.o. mg/kg | Inhibition of gastric acid secretion, percentage | Therapeutic index |
| 5 | 70 | about 50 | 28.6 |
|   | 100 | 93 |   |
| 27 | 50 | 33 |   |
|   | 62 | about 50 | 32.3 |
|   | 100 | 82 |   |
| 36 | 50 | 30 |   |
|   | 65 | about 50 | 27.7 |
|   | 100 | 73 |   |
| atropine ($LD_{50}$ = 200 mg/kg) | 50 | about 45 | 4 |
| proglumide ($LD_{50}$ = 2775 mg/kg) | 200 | about 20 | 11.4 |
| cimetidine ($LD_{50}$ = 470 mg/kg) | 50 | 45 | 9.4 |

The antiperistaltic effect of the compounds of the invention was examined on groups of mice consisting of 10 animals. Each dosis of the compound to be tested was administered to one group, orally, 60 minutes prior to the administration of a 10 percent carbon suspension. 20 minutes after the administration of the carbon suspension, the animals were sacrificed and the length of the entire small intestine as well as that of the small intestine filled with carbon were determined. The reference substance used was papaverine [1-(3,4-dimethoxybenzyl)-6,7-dimethoxyisoquinoline]. The results obtained are summarized in Table IV.

TABLE IV

| Antiperistaltic effect | | |
|---|---|---|
| Compound (No. of Example) | $ED_{50}$ p.o. mg/kg | Therapeutic index |
| 1 | 18 | 111 |
| 3 | 400 | 5 |
| 5 | 400 | 5 |
| 9 | 400 | 5 |
| 27 | 50 | 40 |
| 31 | 50 | 40 |
| 33 | 45 | 45 |
| 34 | 60 | 33 |
| 35 | 145 | 14 |
| 36 | 360 | 5 |
| papaverine | 180 | 3.4 |

The compounds of the general formula I as well as the acid addition salts thereof can be employed as active substances in pharmaceutical compositions having primarily analgesic effect. The pharmaceutical products are prepared by admixing the novel compounds of the general formula I or their acid addition salts with carriers usable in the pharmaceutical industry and transforming the mixture obtained into pharmaceutical products. A typical dose for adult patients is 1 to 1000 mg/kg, especially 2 to 500 mg/kg.

Preferable pharmaceutical products for oral administration, such as tablets, capsules, coated tablets, solutions, suspensions, etc. or for parenteral administration, such as sterile solutions or suspensions are prepared.

Carriers in the solid pharmaceutical products may be binding agents such as gelatin, sorbitol, polyvinylpyrrolidone, filling agents, such as lactose, sugar, starch, calcium phosphate, auxiliary agents for tabletting, such as magnesium stearate, polyethyleneglycol, silica, wetting agents, such as sodium laurylsulfate, etc.

Carriers in the liquid pharmaceutical products may be suspending agents, such as sorbitol, sugar solution, gelatin, carboxymethylcellulose, emulsifying agents, such as sorbitan monooleate, solvents, such as oils, glycine, propyleneglycol, ethanol, preservatives, such as methyl-p-hydroxybenzoate, propyl-p-hydroxybenzoate, etc.

If desired, the pharmaceutical products may contain known flavouring and colouring agents, too.

Further details of the invention are illustrated by the following non-limiting Examples.

EXAMPLE 1

1-Nitropyrazolo[1,5-c]quinazoline

A. 5-(o-Aminophenyl)-4-nitropyrazole

A mixture of 20.8 g (0.1 mole) of 4-chloro-3-nitroquinoline, 40 ml of benzene and 40 ml of hydrazine hydrate is refluxed for 2 hours, then cooled. The separated phase containing hydrazine hydrate is diluted with 150 ml of water. Yellow-white crystals separate. Thus, 16.8 g (83%) of 5-(o-aminophenyl)-4-nitropyrazole are obtained. M.p.: 175°–176° C. (ethanol).

B. 1-Nitropyrazolo[1,5-c]quinazoline

A mixture of 20.4 g (0.1 mole) of 5-(o-aminophenyl)-4-nitropyrazole, 250 ml of triethyl orthoformate and 0.1 g of p-toluenesulfonic acid is heated at 120° to 130° C. for 2 hours. The ethanol formed during the reaction is continuously distilled off. On heating the dark brown solution obtained, 19.7 g (92%) of 1-nitropyrazolo[1,5-c]quinazoline separates. M.p.: 177°–178° C.

EXAMPLE 2

1-Nitro-5-phenylpyrazolo[1,5-c]quinazoline 20.4 g (0.1 mole) of 5-(o-aminophenyl)-4-nitropyrazole are dissolved in 200 ml of pyridine. To the solution obtained, 14.0 g (0.1 mole) of benzoyl chloride are added, drop by drop, and the temperature of the reaction mixture is increased by 10° to 15° C., spontaneously. The mixture is reacted for 2 hours, then poured into water, and the product that solidifies is filtered off and recrystallized from dichloroethane. Thus, 12.5 g (43%) of 1-nitro-5-phenylpyrazolo[1,5-c]quinazoline are obtained. M.p.: 187°–188° C.

EXAMPLE 3

1-Nitro-5-methylpyrazolo[1,5-c]quinazoline 20.4 g (0.1 mole) of 5-(o-aminophenyl)-4-nitropyrazole are heated with 100 ml of acetic anhydride for 2 hours under reflux. The solution obtained is poured into water, the precipitate that solidifies is filtered off, washed with water, dried, then boiled in a ten times' quantity of xylene for 5 hours. Thus, 11.4 g (50%) of 1-nitro-5-methylpyrazolo[1,5-c]quinazoline are obtained. M.p.: 178°–179° C.

EXAMPLE 4

1-Aminopyrazolo[1,5-c]quinazoline 21.4 g (0.1 mole) of 1-nitropyrazolo[1,5-c]quinazoline are treated with hydrogen in ethanol and in the presence of palladium/carbon at room temperature and atmospheric pressure. When the hydrogen consumption ceases, the solution is filtered and evaporated. 14.7 g (80%) of 1-aminopyrazolo[1,5-c]quinazoline are obtained. M.p.: 168°–170° C.

EXAMPLE 5

1-Acetaminopyrazolo[1,5-c]quinazoline 19.8 g (0.1 mole) of 1-aminopyrazolo[1,5-c]quinazoline are boiled with 100 ml of acetic anhydride for 1 hour. On cooling the product separates. After filtration, washing and drying, 22.0 g (90%) of 1-acetaminopyrazolo[1,5-c]quinazoline are obtained. M.p.: 256°–258° C.

EXAMPLE 6

1-Propionylaminopyrazolo[1,5-c]quinazoline

Example 5 is repeated with the exception that, instead of acetic anhydride, propionic anhydride is employed. 1-Propionylaminopyrazolo[1,5-c]quinazoline is obtained. M.p.: 202°–204° C.

EXAMPLE 7

1-Benzylideneimino-5-methylpyrazolo[1,5-c]quinazoline 3.96 g (0.02 mole) of 1-amino-5-methylpyrazolo[1,5-c]quinazoline are dissolved in 45 ml of ethanol. 2.12 g (0.02 mole) of benzaldehyde are added and the solution is heated to boiling. The precipitate is filtered off after cooling and washed with ethanol. 5.0 g (87.5%) 1-benzylideneimino-5-methylpyrazolo-[1,5-c]quinazoline are obtained. M.p.: 180°–181° C.

EXAMPLE 8

1-Isopropylideneiminopyrazolo[1,5-c]quinazoline 1.85 g (0.01 mole) of 1-aminopyrazolo[1,5-c]quinazoline are heated with 25 ml of acetone under reflux for 3 hours. The reaction mixture is evaporated to dryness to give 2.14 g (97%) of 1-isopropylideneiminopyrazolo[1,5-c]quinazoline. M.p.: 87°–89° C.

EXAMPLE 9

1-Nitro-5,5-dimethyl-5,6-dihydropyrazolo[1,5-c]quinazoline

A mixture of 20.4 g (0.1 mole) of 5-(o-aminophenyl)-4-nitropyrazole, 300 ml of acetone and 0.3 ml of acetic acid is heated under reflux for 1 hour. After evaporation, 24.0 g (98.5%) of 1-nitro-5,5-dimethyl-5,6-dihydropyrazolo[1,5-c]quinazoline are obtained. M.p.: 193°–195° C.

EXAMPLE 10

1-Nitro-5,5-diethyl-5,6-dihydropyrazolo[1,5-c]quinazoline

Example 9 is repeated with the exception that, instead of acetone, diethylketone is used. 1-Nitro-5,5-diethyl-5,6-dihydropyrazolo[1,5-c]quinazoline is obtained. M.p.: 132°–134° C. Yield: 97%.

EXAMPLE 11

1-Nitro-5-methyl-5,6-dihydropyrazolo[1,5-c]quinazoline 20.4 g (0.1 mole) of 5-(o-aminophenyl)-4-nitropyrazole are dissolved in a mixture of 250 ml of water, 400 ml of acetic acid and 175 ml of ethanol, then 10 ml (about 0.1 mole) of acetaldehyde in 10 ml of ethanol are added. Yellow crystals separate, immediately. Thus, 21.0 g (92%) of 1-nitro-5-methyl-5,6-dihydropyrazolo[1,5-c]quinazoline are obtained. M.p.: 173°–175° C.

EXAMPLE 12

1-Nitro-5,6-dihydropyrazolo[1,5-c]quinazoline

Example 11 is repeated with the exception that, instead of acetaldehyde, 40 percent aqueous formaldehyde is employed. 1-Nitro-5,6-dihydropyrazolo[1,5-c]quinazoline is obtained. M.p.: 156°–157° C. Yield: 83%.

EXAMPLE 13

1-Nitro-5-phenyl-5,6-dihydropyrazolo[1,5-c]quinazoline

Example 11 is repeated with the exception that, instead of acetaldehyde, benzaldehyde is used. 1-Nitro-5-phenyl-5,6-dihydropyrazolo[1,5-c]quinazoline is obtained. M.p.: 157°–158° C. Yield: 82.5%.

EXAMPLE 14 spiro(Cyclopentane-1,5')-1-nitro-5,6-dihydropyrazolo[1,5-c]quinazoline 5-(o-Aminophenyl)-4-nitropyrazole is reacted with cyclopentanone as described in Example 11. spiro(Cyclopentane-1,5')-1-nitro-5,6-dihydropyrazolo[1,5-c]quinazoline is obtained with a yield of 86%. M.p.: 197°–198° C.

EXAMPLE 15 spiro(Cyclohexane-1,5')-1-nitro-5,6-dihydropyrazolo[1,5-c]quinazoline 5-(o-Aminophenyl)-4-nitropyrazole is reacted with cyclohexanone as given in Example 11. spiro(Cyclohexane-1,5')-1-nitro-5,6-dihydropyrazolo[1,5-c]quinazoline is obtained. M.p.: 157°–158° C. Yield: 82%.

EXAMPLE 16 spiro(Cycloheptane-1,5')-1-nitro-5,6-dihydropyrazolo[1,5-c]quinazoline 5-(o-Aminophenyl)-4-nitropyrazole is reacted with cycloheptanone as described in Example 11. spiro(Cycloheptane-1,5')-1-nitro-5,6-dihydropyrazolo[1,5-c]quinazoline is obtained. M.p.: 183°–184° C. Yield: 84%.

EXAMPLE 17 spiro(Cyclooctane-1,5')-1-nitro-5,6-dihydropyrazolo[1,5-c[quinazoline 5-(o-Aminophenyl)-4-nitropyrazole is reacted with cyclooctanone as described in Example 11. spiro(Cyclooctane-1,5')-1-nitro-5,6-dihydropyrazolo[1,5-c]quinazoline is obtained with a yield of 77%. M.p.: 166°–168° C.

EXAMPLE 18

1-Nitro-5-(p-methoxyphenyl)-5,6-dihydropyrazolo[1,5-c]quinazoline 5-(o-Aminophenyl)-4-nitropyrazole is reacted with p-anisaldehyde as given in Example 11. 1-Nitro-5-(p-methoxyphenyl)-5,6-dihydropyrazolo[1,5-c]quinazoline is obtained with a yield of 97%. M.p.: 181°–183° C.

EXAMPLE 19

1-Nitro-5-(o-hydroxyphenyl)-5,6-dihydropyrazolo[1,5-c]quinazoline 5-(o-Aminophenyl)-4-nitropyrazole is reacted with salicylaldehyde as described in Example 11. 1-Nitro-5-(o-hydroxyphenyl)-5,6-dihydropyrazolo[1,5-c]quinazoline is obtained with a yield of 76%. M.p.: 235°–237° C.

EXAMPLE 20

1-Nitro-5-(p-nitrophenyl)-5,6-dihydropyrazolo[1,5-c]quinazoline 5-(o-Aminophenyl)-4-nitropyrazole is reacted with p-nitrobenzaldehyde as described in Example 11. 1-Nitro-5-(p-nitrophenyl)-5,6-dihydropyrazolo[1,5-c]quinazoline is obtained. M.p.: 190°–191° C. Yield: 90%.

EXAMPLE 21

1-Nitro-5-(p-chlorophenyl)-5,6-dihydropyrazolo[1,5-c]quinazoline 5-(o-Aminophenyl)-4-nitropyrazole is reacted with p-chlorobenzaldehyde as described in Example 11 to give 1-nitro-5-(p-chlorophenyl)-5,6-dihydropyrazolo[1,5-c]quinazoline. M.p.: 217°–219° C. Yield: 83%.

EXAMPLE 22

1-Nitro-5-(p-dimethylaminophenyl)-5,6-dihydropyrazolo[1,5-c]quinazoline 5-(o-Aminophenyl)-4-nitropyrazole is reacted with p-dimethylaminobenzaldehyde as described in Example 11 to give 1-nitro-5-(p-dimethylaminophenyl)-5,6-dihydropyrazolo[1,5-c]quinazoline with a yield of 72%. M.p.: 190°–192° C.

EXAMPLE 23

1-Nitro-5-hexyl-5-methyl-5,6-dihydropyrazolo[1,5-c]quinazoline 5-(o-Aminophenyl)-4-nitropyrazole is reacted with n-hexyl methyl ketone as given in Example 11 to give 1-nitro-5-hexyl-5-methyl-5,6-dihydropyrazolo[1,5-c]quinazoline. M.p.: 86°–88° C. Yield: 81.5%.

EXAMPLE 24

1-Nitro-5-propenyl-5,6-dihydropyrazolo[1,5-c]quinazoline 5-(o-Aminophenyl)-4-nitropyrazole is reacted with crotonaldehyde as described in Example 11 to give 1-nitro-5-propenyl-5,6-dihydropyrazolo[1,5-c]quinazoline. M.p.: 115°–117° C. Yield: 83%.

EXAMPLE 25

1-Nitro-5-styryl-5,6-dihydropyrazolo[1,5-c]quinazoline 5-(o-Aminophenyl)-4-nitropyrazole is reacted with cinnamaldehyde as described in Example 11 to give 1-nitro-5-styryl-5,6-dihydropyrazolo[1,5-c]quinazoline. M.p.: 171°–173° C. Yield: 85.5%.

EXAMPLE 26

1-Nitro-5,6-dihydropyrazolo[1,5-c]quinazoline-5-carboxylic acid 5-(o-Aminophenyl)-4-nitropyrazole is reacted with glyoxylic acid as described in Example 11 to give 1- nitro-5,6-dihydropyrazolo[1,5-c]quinazoline-5-carboxylic acid with a yield of 69%. M.p.: 203°–205° C.

EXAMPLE 27

1-Nitro-5-methyl-6-acetyl-5,6-dihydropyrazolo[1,5-c]quinazoline 22.9 g (0.1 mole) of 1-nitro-5-methyl-5,6-dihydropyrazolo[1,5-c]quinazoline is boiled with 120 ml of acetic anhydride for 1 hour, then the solution obtained is poured into water. The product that solidifies is filtered off, washed with water and dried. Thus, 25.0 g (83%) of 1-nitro-5-methyl-6-acetyl-5,6-dihydropyrazolo[1,5-c]quinazoline are obtained. M.p.: 149°–150° C.

EXAMPLE 28

1-Nitro-5-phenyl-6-acetyl-5,6-dihydropyrazolo[1,5-c]quinazoline

1-Nitro-5-phenyl-5,6-dihydropyrazolo[1,5-c]quinazoline is treated with acetic anhydride as described in Example 27 to give 1-nitro-5-phenyl-6-acetyl-5,6-dihydropyrazolo[1,5-c]quinazoline. M.p.: 156°–157° C. Yield: 92%.

EXAMPLE 29

1-Nitro-5-(p-chlorophenyl)-6-acetyl-5,6-dihydropyrazolo[1,5-c]quinazoline

1-Nitro-5-(p-chlorophenyl)-5,6-dihydropyrazolo[1,5-c]quinazoline is treated with acetic anhydride as described in Example 27 to give 1-nitro-5-(p-chlorophenyl)-6-acetyl-5,6-dihydropyrazolo[1,5-c]quinazoline with a yield of 95%. M.p.: 183°–184° C.

EXAMPLE 30

1-Nitro-5-(p-methoxyphenyl)-6-acetyl-5,6-dihydropyrazolo[1,5-c]quinazoline

1-Nitro-5-(p-methoxyphenyl)-5,6-dihydropyrazolo[1,5-c]quinazoline is reacted with acetic anhydride as described in Example 27 to give 1-nitro-5-(p-methoxyphenyl)-6-acetyl-5,6-dihydropyrazolo[1,5-c]quinazoline with a yield of 99%. M.p.: 153°–154° C.

EXAMPLE 31

1-Nitro-5,5-dimethyl-6-acetyl-5,6-dihydropyrazolo[1,5-c]quinazoline

1-Nitro-5,5-dimethyl-5,6-dihydropyrazolo[1,5-c]quinazoline is treated with acetic anhydride to give 1-nitro-5,5-dimethyl-6-acetyl-5,6-dihydropyrazolo[1,5-c]quinazoline with a yield of 69%. M.p.: 182°–183° C.

EXAMPLE 32

1-Amino-5,5-dimethyl-5,6-dihydropyrazolo[1,5-c]quinazoline 3.8 g (0.015 mole) of 1-nitro-5,5-dimethyl-5,6-dihydropyrazolo[1,5-c]quinazoline is reduced with hydrogen in ethanol in the presence of palladium/carbon. When the hydrogen consumption ceases, the catalyst is removed and the solvent is evaporated. Thus, 2.42 g (76%) of 1-amino-5,5-dimethyl-5,6-dihydropyrazolo[1,5-c]quinazoline are obtained. M.p.: 181°–183° C. The hydrochloride can be precipitated by treating the free amine in ethanol with anhydrous hydrogen chloride dissolved in ethyl acetate. M.p.: 244°–245° C.

EXAMPLE 33

1-Acetamino-5,5-dimethyl-5,6-dihydropyrazolo[1,5-c]quinazoline 16.1 g (0.075 mole) of 1-amino-5,5-dimethyl-5,6-dihydropyrazolo[1,5-c]quinazoline are dissolved in 100 ml of pyridine. 80 ml of acetic anhydride are added and the reaction mixture is left to stand at room temperature for 1 day. The crystals separated spontaneously are filtered off and the mother liquor is evaporated. The collected crystals are washed with water and dried. Thus, 16.7 g (82%) of 1-acetamino-5,5-dimethyl-5,6-dihydropyrazolo[1,5-c]quinazoline are obtained. M.p.: 228°–230° C.

EXAMPLE 34

1-Acetamino-5,5-dimethyl-6-acetamino-5,6-dihydropyrazolo[1,5-c]quinazoline 28.6 g (0.1 mole) of 1-nitro-5,5-dimethyl-6-acetyl-5,6-dihydropyrazolo[1,5-c]quinazoline are hydrogenated in ethanol in the presence of palladium/carbon catalyst. When the reduction is complete, the catalyst is removed by filtration and the solution obtained is evaporated in an inert atmosphere. Thus, 24.4 g (95%) of amine are obtained as an oil. It is dissolved in 250 ml of pyridine, 150 ml of acetic anhydride are added and the mixture is left to stand at room temperature for 1 day. The white crystals separated are filtered and the mother liquor is evaporated. The product is washed with water and dried. 26.0 g (88%) of 1-acetamino-5,5-dimethyl-6-acetamino-5,6-dihydropyrazolo[1,5-c]quinazoline are obtained. M.p.: 229°–230° C.

EXAMPLE 35

1-Acetamino-5-methyl-6-acetyl-5,6-dihydropyrazolo[1,5-c]quinazoline 20.5 g (0.08 mole) of 1-amino-5-methyl-6-acetyl-5,6-dihydropyrazolo[1,5-c]quinazoline are dissolved in 400 ml of pyridine. 100 ml of acetic anhydride are added and the solution is left to stand at room temperature for 10 hours. A portion of the product separates as a crystalline substance, the remaining portion is separated by evaporating the mother liquor. 21.1 g (90%) of 1-acetamino-5-methyl-6-acetyl-5,6-dihydropyrazolo[1,5-c]quinazoline are obtained. M.p.: 218°–220° C.

EXAMPLE 36

1-Acetamino-5-methylpyrazolo[1,5-c]quinazoline

1-Amino-5-methylpyrazolo[1,5-c]quinazoline is treated with acetic anhydride as described in Example 5 to give 1-acetamino-5-methylpyrazolo[1,5-c]quinazoline. M.p.: 258°–260° C. Yield: 89%.

EXAMPLE 37

1-Amino-5-methyl-6-acetyl-5,6-dihydropyrazolo[1,5-c]quinazoline 27.1 g (0.1 mole) of 1-nitro-5-methyl-6-acetyl-5,6-dihydropyrazolo[1,5-c]quinazoline are hydrogenized in ethanol in the presence of palladium/carbon catalyst. When the reduction is complete, the catalyst is removed by filtration and the filtrate is evaporated in an inert atmosphere under reduced pressure. 20.5 g (81%) of 1-amino-5-methyl-6-acetyl-5,6-dihydropyrazolo[1,5-c]quinazoline are obtained as white crystals. M.p.: 170°–172° C.

EXAMPLE 38

1-Nitro-5-undecyl-5,6-dihydropyrazolo[1,5-c]quinazoline 5-(o-Aminophenyl)-4-nitropyrazole is reacted with dodecyl aldehyde as described in Example 11 to give 1-nitro-5-undecyl-5,6-dihydropyrazolo[1,5-c]quinazoline with a yield of 60%. M.p.: 92°–93° C.

EXAMPLE 39

1-Nitro-5-undecyl-6-acetyl-5,6-dihydropyrazolo[1,5-c]quinazoline

1-Nitro-5-undecyl-5,6-dihydropyrazolo[1,5-c]quinazoline is treated with acetic anhydride as described in Example 27 to give 1-nitro-5-undecyl-6-acetyl-5,6-dihydropyrazolo[1,5-c]quinazoline. M.p.: 83°–85° C. Yield: 85%.

EXAMPLE 40

1-Nitro-6-methyl-5,6-dihydropyrazolo[1,5-c]quinazoline 2.15 g (0.01 mole) of 1-nitro-5,6-dihydropyrazolo[1,5-c]quinazoline are dissolved in a mixture of 10 ml of ethanol and 20 ml of methyl iodide. 10 ml of triethylamine are added to the boiled mixture. The reaction mixture is boiled for 8 hours, then evaporated to dryness, the residue is dissolved in chloroform, washed with water, dried and evaporated. Thus, 2.0 g (87%) of 1-nitro-6-methyl-5,6-dihydropyrazolo[1,5-c]quinazoline are obtained. M.p.: 172°–173° C.

EXAMPLE 41

1-Nitro-5-cyclohexyl-5,6-dihydropyrazolo[1,5-c]quinazoline 5-(o-Aminophenyl)-4-nitropyrazole is reacted with hexahydrobenzaldehyde as described in Example 11 to give 1-nitro-5-cyclohexyl-5,6-dihydropyrazolo[1,5-c]quinazoline. M.p.: 150°–152° C. Yield: 73.8%.

What we claim is:

1. A pyrazolo quinazoline of the formula

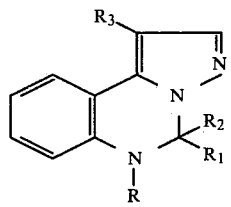

wherein
R represents a hydrogen atom, a $C_{1-4}$ alkyl group or a $C_{1-4}$ alkanoyl group,
$R_1$ is a hydrogen atom, a $C_{1-12}$ alkyl group, a $C_{3-8}$ cycloalkyl group, a $C_{2-4}$ alkenyl group, a phenylalkenyl group, wherein the alkenyl group has 2 to 4 carbon atoms, a carboxy group or a phenyl group optionally substituted by a halogen atom, a nitro group, a hydroxy group, a $C_{1-4}$ alkoxy group or a di($C_{1-4}$ alkyl)amino group, or
R and $R_1$ may form together a valence bond,
$R_2$ represents a hydrogen atom, a $C_{1-4}$ alkyl or a phenyl group, or
$R_1$ and $R_2$ may form together a $C_{2-7}$ alkylene group, and
$R_3$ represents a nitro group, an amino group, an alkanoylamino group, wherein the alkanoyl group has 1 to 4 carbon atoms, a benzylideneimino group or an alkylideneimino group, wherein the alkylidene group has 1 to 4 carbon atoms,
and pharmaceutically acceptable acid addition salts thereof.

2. A nitropyrazolo[1,5-c]quinazoline of the formula

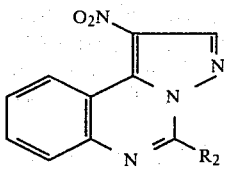

wherein $R_2$ represents a hydrogen atom or a $C_{1-4}$ alkyl group, and pharmaceutically acceptable acid addition salts thereof.

3. An aminopyrazolo[1,5-c]quinazoline of the formula

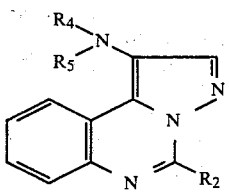

wherein
$R_2$ represents a hydrogen atom or a $C_{1-4}$ alkyl group,
$R_4$ stands for a $C_{1-4}$ alkanoyl group and
$R_5$ is a hydrogen atom
and pharmaceutically acceptable acid addition salts thereof.

4. A nitropyrazolo[1,5-c]quinazoline of the formula

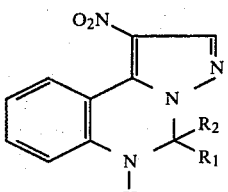

wherein $R_1$ and $R_2$ represent hydrogen, and pharmaceutically acceptable acid addition salts thereof.

5. A nitropyrazolo[1,5-c]quinazoline of the formula

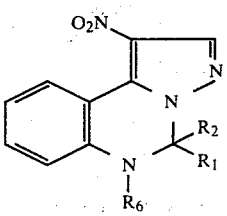

wherein
$R_1$ represents a $C_{1-4}$ alkyl group,
$R_2$ represents a hydrogen atom or a $C_{1-4}$ alkyl group,
$R_6$ represents a $C_{1-4}$ alkanoyl group,
and pharmaceutically acceptable acid addition salts thereof.

6. An aminopyrazolo[1,5-c]quinazoline of the formula

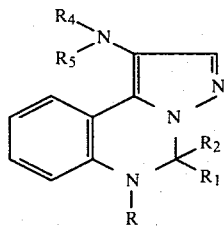

wherein

R represents a hydrogen atom or a $C_{1-4}$ alkanoyl group, $R_1$ and $R_2$ each represents a $C_{1-4}$ alkyl group, $R_4$ stands for a $C_{1-4}$ alkanoyl group, $R_5$ is a hydrogen atom, and pharmaceutically acceptable acid addition salts thereof.

7. 1-Nitropyrazolo[1,5-c]quinazoline.
8. 1-Nitro-5-methylpyrazolo[1,5-c]quinazoline.
9. 1-Acetaminopyrazolo[1,5-c]quinazoline.
10. 1-Nitro-5-methyl-6-acetyl-5,6-dihydropyrazolo[1,5-c]quinazoline.
11. 1-Nitro-5,5-dimethyl-6-acetyl-5,6-dihydropyrazolo[1,5-c]quinazoline.
12. 1-Acetamino-5,5-dimethyl-5,6-dihydropyrazolo[1,5-c]quinazoline.
13. 1-Acetamino-5,5-dimethyl-6-acetyl-5,6-dihydropyrazolo[1,5-c]quinazoline.
14. 1-Acetamino-5-methyl-6-acetyl-5,6-dihydropyrazolo[1,5-c]quinazoline.
15. 1-Acetamino-5-methylpyrazolo[1,5-c]quinazoline.
16. An analgesic composition comprising an analgesically effective amount of a compound of claim 1 and a pharmaceutical carrier.

* * * * *